(12) United States Patent
Smith et al.

(10) Patent No.: US 7,491,666 B2
(45) Date of Patent: Feb. 17, 2009

(54) LATENT ELASTIC ARTICLES AND METHODS OF MAKING THEREOF

(75) Inventors: Charles Allen Smith, Cumming, GA (US); Patricia Hwang Calhoun, Alpharetta, GA (US); James Russell Fitts, Jr., Gainesville, GA (US); Janis Wilson Hughes, Alpharetta, GA (US); Tamara Lee Mace, Marietta, GA (US); Glynis Allicia Walton, Roswell, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 201 days.

(21) Appl. No.: 11/119,486

(22) Filed: Apr. 29, 2005

(65) Prior Publication Data
US 2006/0246803 A1 Nov. 2, 2006

(51) Int. Cl.
D04H 1/74 (2006.01)
B32B 5/18 (2006.01)
A61F 13/15 (2006.01)

(52) U.S. Cl. .................. 442/366; 442/373; 604/358

(58) Field of Classification Search .............. 442/366, 442/373
See application file for complete search history.

(56) References Cited

U.S. PATENT DOCUMENTS

| | | |
|---|---|---|
| 3,692,618 A | 9/1972 | Dorschner et al. |
| 3,849,241 A | 11/1974 | Butin et al. |
| 3,855,046 A | 12/1974 | Hansen et al. |
| 4,100,324 A | 7/1978 | Anderson et al. |
| 4,340,563 A | 7/1982 | Appel et al. |
| 4,374,888 A | 2/1983 | Bornslaeger |
| 4,663,220 A | 5/1987 | Wisneski et al. |
| 4,704,116 A | 11/1987 | Enloe |
| 4,720,415 A | 1/1988 | Vander Wielen et al. |
| 4,781,966 A | 11/1988 | Taylor |
| 4,787,699 A | 11/1988 | Moulin |
| 4,798,603 A | 1/1989 | Meyer et al. |
| 4,803,117 A | 2/1989 | Daponte |
| 4,818,464 A | 4/1989 | Lau |

(Continued)

FOREIGN PATENT DOCUMENTS

EP 0971667 B1 12/2002

(Continued)

OTHER PUBLICATIONS

Affinity EG 8185, Polyolefin Plastomer Product Information, Dow Plastics, The Dow Chemical Company, Published Jan. 2005, 2 pages.

*Primary Examiner*—Lynda Salvatore
(74) *Attorney, Agent, or Firm*—Richard M. Shane (57) ABSTRACT

A composite nonwoven fabric having latent elasticity is provided having a latently elastic core comprising a first component that includes a thermoplastic elastomer and a second component that includes a single site catalyzed polyolefin, and at least one gatherable facing material laminated to the elastic core. The first and second components may be, for example, in the form of alternating filaments of styrenic block copolymer and single site catalyzed polyolefin or in the form of conjugate filaments having a first section of styrenic block copolymer and a second section of single site catalyzed polyolefin. Also disclosed are methods of making the latently elastic stretch bonded laminates and personal care articles containing the latently elastic stretch bonded laminates.

8 Claims, 6 Drawing Sheets

U.S. PATENT DOCUMENTS

| | | | |
|---|---|---|---|
| 4,842,596 A | 6/1989 | Kielpikowski et al. |
| 4,940,464 A | 7/1990 | Van Gompel et al. |
| 5,108,820 A | 4/1992 | Kaneko et al. |
| 5,176,668 A | 1/1993 | Bernardin |
| 5,176,672 A | 1/1993 | Bruemmer et al. |
| 5,192,606 A | 3/1993 | Proxmire et al. |
| 5,336,552 A | 8/1994 | Strack et al. |
| 5,382,400 A | 1/1995 | Pike et al. |
| 5,385,775 A | 1/1995 | Wright |
| 5,399,219 A | 3/1995 | Roessler et al. |
| 5,490,846 A | 2/1996 | Ellis et al. |
| 5,509,915 A | 4/1996 | Hanson et al. |
| 5,540,796 A | 7/1996 | Fries |
| 5,595,618 A | 1/1997 | Fries et al. |
| 5,750,444 A | 5/1998 | Jarrell et al. |
| 5,766,389 A | 6/1998 | Brandon et al. |
| 5,914,184 A | 6/1999 | Morman |
| 5,931,823 A | 8/1999 | Stokes et al. |
| 6,645,190 B1 | 11/2003 | Olson et al. |
| 6,761,711 B1 | 7/2004 | Fletcher et al. |
| 6,969,441 B2 | 11/2005 | Welch et al. |
| 2002/0104608 A1 | 8/2002 | Welch et al. |
| 2003/0232928 A1 | 12/2003 | Atwood et al. |
| 2004/0091693 A1* | 5/2004 | Thomas et al. ........... 428/317.9 |

FOREIGN PATENT DOCUMENTS

| | | |
|---|---|---|
| WO | WO 95/16425 | 6/1995 |
| WO | WO 98/29251 | 7/1998 |
| WO | WO 99/65442 | 12/1999 |
| WO | WO 01/32116 | 5/2001 |
| WO | WO 01/87589 | 11/2001 |
| WO | WO 2004/061181 | 7/2004 |

* cited by examiner

LATENT ELASTIC ARTICLES AND METHODS OF MAKING THEREOF

BACKGROUND OF THE INVENTION

Articles requiring a degree of elasticity have been formed by combining elastic core materials with inelastic, or less elastic, facing materials through various lamination processes. Often, such composite laminate articles will be stretchable because of the presence of the elastic core material and the particular manner in which the elastic core and inelastic facing materials have been bonded together during the laminating process.

Typically, such stretchable laminates are formed by joining the inelastic facing material to the elastic core material while the elastic core material or sheet is in a stretched condition. After such joining of the materials, the laminated article is then allowed to relax, which results in the inelastic component gathering in the spaces between bonding sites on the elastic sheet. The resulting laminate article is then stretchable to the extent that the inelastic material gathered between the bond locations allows the elastic material to elongate. Examples of these types of composite stretch bonded laminate articles and materials are set forth in U.S. Pat. Nos. 4,720,415 and 5,385,775, each of which is incorporated herein by reference thereto.

In some stretchable laminate articles, the elastic core material includes elastic strands of continuous filaments that are bonded to the relatively inelastic facing sheet materials while the elastic strands are in a stretched condition. Such elastic continuous filaments may, in certain articles, be sandwiched between two or more relatively inelastic sheets. The relatively inelastic sheets may include nonwoven webs formed by melt-blowing or spunbonding various polymers. Examples of such laminates and processes for making are shown in U.S. Pat. No. 5,385,775 to Wright and copending U.S. Patent Application Publication 2002/0104608A1 to Welch et al., each of which is incorporated herein in its entirety by reference thereto.

Such laminated articles may be utilized in various products requiring a certain degree of stretchability and elasticity, such as diapers, garments, drapes, pads, and the like. In producing the various products that utilize stretchable elastic laminated articles, the elastic laminated articles are unwound from large rolls of material upon which the laminated articles are stored. The stretchable nature of the laminated articles can result in problems during the manufacturing process of the ultimate products. For example, the force required to unwind the rolled articles can at least partially extend the elastic laminate while the elastic article is in tension. This partial extension of the stretchable laminate can make it difficult to properly measure and position the desired quantity of the elastic article in the final product. Therefore, there remains a need in the art for low cost elastic laminate materials that have less than the final desired stretch during the process of cutting and placing the material in a final product, but which achieve the desired level of stretch after having been placed in the final product.

SUMMARY OF THE INVENTION

The present invention provides a composite nonwoven fabric having latent elasticity. The composite nonwoven fabric includes a latently elastic core including a first component that includes a thermoplastic elastomer and a second component that includes a single site catalyzed polyolefin. The composite nonwoven fabric further includes at least one gatherable facing material laminated to the elastic core. The thermoplastic elastomer may include a styrenic block copolymer.

In one embodiment, the first component includes first filaments that include a styrenic block copolymer and second filaments that include the single site catalyzed polyolefin. The first filaments may be continuous filaments substantially oriented in a machine direction of the latently elastic core. Further, the second filaments may be continuous filaments substantially oriented in a machine direction of the latently elastic core. Alternatively, the second filaments may be melt-blown filaments.

In another embodiment, the latently elastic core may include continuous conjugate filaments that include a styrenic block copolymer and a single site catalyzed polyolefin.

In a further embodiment, a personal care product may include one of the composite nonwoven fabrics described above. For example, the personal care product may include diapers, training pants, swimwear, absorbent underpants, adult incontinence products, and feminine hygiene products, such as feminine care pads, napkins and pantiliners.

In another embodiment, a process of making a composite nonwoven fabric having latent elasticity includes the steps of a) extruding an elastic core nonwoven including a thermoplastic elastomer and a single site catalyzed polyolefin; b) quenching and stretching the elastic core nonwoven; c) providing at least one gatherable facing material; and d) laminating the elastic core nonwoven to the gatherable facing material to form the composite nonwoven fabric having latent elasticity. The process may further comprise the steps of providing a second gatherable facing material and laminating the elastic core nonwoven with the first and second gatherable facing materials to form the composite nonwoven fabric having latent elasticity. In one aspect, the process may further comprise the step of applying an adhesive on the surface of one or both of the gatherable facing materials prior to laminating the elastic core nonwoven to the gatherable facing material. In one embodiment, the adhesive may be sprayed on the surface of one or both of the gatherable facing materials.

In a further embodiment, a process for making a personal care product includes the steps of: a) providing a composite nonwoven fabric having latent elasticity that includes a latently elastic core including a thermoplastic elastomer and a single site catalyzed polyolefin, and at least one gatherable facing material laminated to the elastic core; b) fastening the composite nonwoven fabric to a personal care product; c) activating the composite nonwoven fabric; and d) allowing the composite nonwoven fabric to retract, thereby increasing the stretchability of the composite nonwoven fabric.

In another embodiment, a composite nonwoven fabric includes a latently elastic core including a first component that includes a thermoplastic elastomer and a second component that includes an elastic polyolefin-based polymer. The composite nonwoven fabric further includes at least one gatherable facing material laminated to the elastic core.

Other objects, advantages and applications of the present invention will be made clear by the following detailed description of embodiments of the invention and the accompanying drawings wherein reference numerals refer to like or equivalent structures.

DEFINITIONS

Within the context of this specification, each term or phrase below will include the following meaning or meanings.

Figure 6:
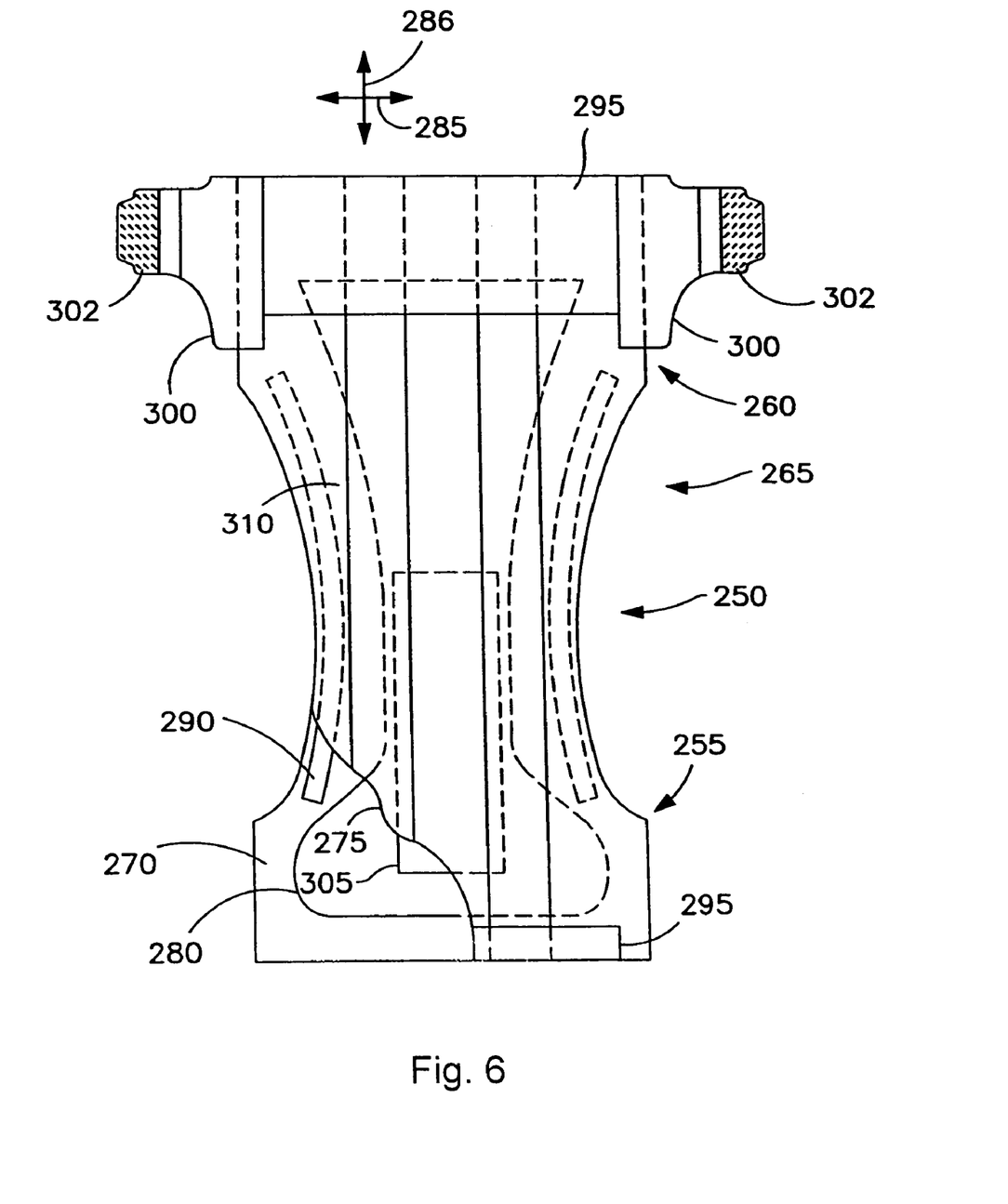
FIG. 6 illustrates a personal care product utilizing a latently elastic stretch bonded laminate made in accordance with the invention.

As used herein, the term "personal care product" means diapers, training pants, swimwear, absorbent underpants, adult incontinence products, and feminine hygiene products, such as feminine care pads, napkins and pantiliners. While a diaper is illustrated in FIG. 6, it should be recognized that the inventive material may just as easily be incorporated in any of the previously listed personal care products as an elastic component. For instance, such material may be utilized to make the elastic side panels of training pants.

The term "continuous filaments", as used herein, refers to strands of continuously formed polymeric filaments. Such filaments will typically be formed by extruding molten material through a die head having a certain type and arrangement of capillary holes therein.

The term "elastic" or "elasticized", as used herein, refers to a material which, upon application of a stretching force, is stretchable to an elongation of at least about 25 percent of its relaxed length, i.e., can be stretched to at least about one and one-quarter times its relaxed length, and upon release of the stretching force will recover at least about 40 percent of the elongation, i.e., will, in the case of 25% elongation, contract to an elongation of not more than about 15%. For example, a 100 centimeter length of material will, under the foregoing definition, be deemed to be elastic if it can be stretched to a length of at least about 125 centimeters and if, upon release of the stretching force, it contracts, in the case of being stretched to 125 cm, to a length of not more than about 115 centimeters. Of course, many elastic materials used in the practice of the invention can be stretched to elongations considerably in excess of 25% of their relaxed length, and many, upon release of the stretching force, will recover to their original relaxed length or very close thereto. For example, some elastic material may be elongated 60 percent, 100 percent, or more, and many of these will recover to substantially their initial relaxed length such as, for example, within 105 percent of their original relaxed length upon release of the stretching force.

As used herein, the term "latent", "latent elasticity", or variation thereof refers to materials having a certain degree of stretchability which are capable of becoming more stretchable upon activation, e.g. by heat activation, microwave, ultrasound, chemical treatment, and so forth. The materials may or may not be elastic prior to activation, but will be elastic after activation.

As used herein, the term "nonelastic" or "inelastic" refers to any material which does not fall within the definition of "elastic" above.

As used herein, the term "polymer" or "polymeric" generally includes, but is not limited to, homopolymers, copolymers, such as, for example, block, graft, random and alternating copolymers, terpolymers, etc. and blends and modifications thereof. Furthermore, the term "polymer" includes all possible geometrical configurations of the material, such as isotactic, syndiotactic and random symmetries.

The term "composite nonwoven fabric", "composite nonwoven", "laminate", or "nonwoven laminate", as used herein, unless otherwise defined, refers to a material having at least one elastic material joined to at least one sheet material. In most embodiments such laminates or composite fabric will have a gatherable layer which is bonded to an elastic layer or material so that the gatherable layer may be gathered between bonding locations. As set forth herein, the composite elastic laminate may be stretched to the extent that the gatherable material gathered between the bond locations allows the elastic material to elongate. This type of composite elastic laminate is disclosed, for example, in U.S. Pat. No. 4,720,415 to Vander Wielen et al., which is incorporated herein in its entirety by reference thereto.

As used herein, the terms "machine direction" or "MD" means the direction along the length of a fabric in the direction in which it is produced. The terms "cross machine direction," "cross directional," or "CD" mean the direction across the width of fabric, i.e. a direction generally perpendicular to the MD.

As used herein, the term "nonwoven web" refers to a web having a structure of individual fibers or threads that are interlaid, but not in an identifiable, repeating manner. Nonwoven webs have been, in the past, formed by a variety of processes such as, for example, meltblowing processes, spunbonding processes and bonded carded web processes.

As used herein, the term "meltblown" or "meltblown fibers" means fibers formed by extruding a molten thermoplastic material through a plurality of fine, usually circular, die capillaries as molten thermoplastic material or filaments into a high velocity gas (e.g. air) stream which attenuates the filaments of molten thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, U.S. Pat. No. 3,849,241 to Butin, which is incorporated herein in its entirety by reference thereto.

As used herein, the term "spunbond" or "spunbonded fibers" refers to small diameter fibers formed by extruding a molten thermoplastic material as filaments from a plurality of fine, usually circular, capillaries of a spinerette with the diameter of the extruded filaments then being rapidly reduced as by, for example, eductive stretching or other well-known spun-bonding mechanisms. The production of spun-bonded nonwoven webs is illustrated in patents such as, for example, U.S. Pat. No. 4,340,563 to Appel et al., and U.S. Pat. No. 3,692,618 to Dorschner et al. The disclosures of these patents are incorporated herein in their entireties by reference thereto.

As used herein, the term "bonded carded webs" refers to webs that are made from staple fibers which are usually purchased in bales. The bales are placed in a fiberizing unit/picker which separates the fibers. Next, the fibers are sent through a combining or carding unit which further breaks apart and aligns the staple fibers in the machine direction so as to form a machine direction-oriented fibrous nonwoven web. Once the web has been formed, it is then bonded by one or more of several bonding methods. One bonding method is powder bonding wherein a powdered adhesive is distributed throughout the web and then activated, usually by heating the web and adhesive with hot air. Another bonding method is pattern bonding wherein heated calender rolls or ultrasonic bonding equipment is used to bond the fibers together, usually in a localized bond pattern through the web and/or alternatively the web may be bonded across its entire surface if so desired. When using bicomponent staple fibers, through-air bonding equipment is, for many applications, especially advantageous.

As used herein, the term "coform" means a process in which at least one meltblown die is arranged near a chute through which other materials are added to the web while it is forming. Such other materials may be pulp, superabsorbent particles, cellulose or staple fibers, for example. Coform processes are shown in U.S. Pat. No. 4,818,464 to Lau and U.S. Pat. No. 4,100,324 to Anderson et al., each incorporated by reference herein in its entirety.

As used herein, the term "conjugate fibers" or "conjugate filaments" refers to fibers or filaments which have been formed from at least two polymer sources extruded from separate extruders but spun together to form one fiber or filament. Conjugate fibers or filaments are also sometimes referred to as multicomponent or bicomponent fibers or filaments. The polymers are usually different from each other though conjugate fibers may be monocomponent fibers. The polymers are arranged in substantially constantly positioned distinct zones across the cross-section of the conjugate fibers and extend continuously along the length of the conjugate fibers. The configuration of such a conjugate fiber may be, for example, a sheath/core arrangement wherein one polymer is surrounded by another or may be a side by side arrangement, a pie arrangement or an "islands-in-the-sea" arrangement. Conjugate fibers or filaments are taught, for example, in U.S. Pat. No. 5,108,820 to Kaneko et al., U.S. Pat. No. 5,336,552 to Strack et al., and U.S. Pat. No. 5,382,400 to Pike et al. For two component fibers or filaments, the polymers may be present in ratios of 75/25, 50/50, 25/75 or any other desired ratios. Polymers useful in forming conjugate fibers include those normally used in other fiber or filament forming processes.

As used herein, the terms "sheet" and "sheet material" shall be interchangeable and in the absence of a word modifier, refer to woven materials, nonwoven webs, polymeric films, polymeric scrim-like materials, and polymeric foam sheeting.

The basis weight of nonwoven fabrics or films is usually expressed in ounces of material per square yard (osy) or grams per square meter (g/m² or gsm) and the fiber diameters are usually expressed in microns. (Note that to convert from osy to gsm, multiply osy by 33.91). Film thicknesses may also be expressed in microns or mil.

As used herein, the term "laminate" refers to a composite structure of two or more sheet material layers that have been adhered through a bonding step, such as through adhesive bonding, thermal bonding, point bonding, pressure bonding, extrusion coating or ultrasonic bonding.

As used herein, the term "thermoplastic" shall refer to a polymer which is capable of being melt processed.

As used herein the term "thermal point bonding" involves passing a fabric or web of fibers to be bonded between a heated calender roll and an anvil roll. The calender roll is usually, though not always, patterned in some way so that the entire fabric is not bonded across its entire surface, and the anvil roll is usually flat. As a result, various patterns for calender rolls have been developed for functional as well as aesthetic reasons. One example of a pattern has points and is the Hansen Pennings or "H&P" pattern with about a 30 percent bond area with about 200 bonds/square inch as taught in U.S. Pat. No. 3,855,046 to Hansen and Pennings, incorporated herein by reference in its entirety. The H&P pattern has square point or pin bonding areas wherein each pin has a side dimension of 0.038 inches (0.965 mm), a spacing of 0.070 inches (1.778 mm) between pins, and a depth of bonding of 0.023 inches (0.584 mm). The resulting pattern has a bonded area of about 29.5 percent. Another typical point bonding pattern is the expanded Hansen Pennings or "EHP" bond pattern which produces a 15 percent bond area with a square pin having a side dimension of 0.037 inches (0.94 mm), a pin spacing of 0.097 inches (2.464 mm) and a depth of 0.039 inches (0.991 mm). Another typical point bonding pattern designated "714" has square pin bonding areas wherein each pin has a side dimension of 0.023 inches, a spacing of 0.062 inches (1.575 mm) between pins, and a depth of bonding of 0.033 inches (0.838 mm). The resulting pattern has a bonded area of about 15 percent. Yet another common pattern is the C-Star pattern which has a bond area of about 16.9 percent. The C-Star pattern has a cross-directional bar or "corduroy" design interrupted by shooting stars. Other common patterns include a diamond pattern with repeating and slightly offset diamonds with about a 16 percent bond area and a wire weave pattern looking as the name suggests, e.g. like a window screen pattern having a bond area in the range of from about 15 percent to about 21 percent and about 302 bonds per square inch.

Typically, the percent bonding area varies from around 10 percent to around 30 percent of the area of the fabric laminate. As is well known in the art, the spot bonding holds the laminate layers together as well as imparts integrity to each individual layer by bonding filaments and/or fibers within each layer.

As used herein, the term "ultrasonic bonding" means a process performed, for example, by passing the fabric between a sonic horn and anvil roll as illustrated in U.S. Pat. No. 4,374,888 to Bornslaeger, incorporated by reference herein in its entirety.

As used herein, the term "adhesive bonding" means a bonding process which forms a bond by application of an adhesive. Such application of adhesive may be by various processes such as slot coating, spray coating and other topical applications. Further, such adhesive may be applied within a product component and then exposed to pressure such that contact of a second product component with the adhesive containing product component forms an adhesive bond between the two components.

As used herein, and in the claims, the term "comprising" is inclusive or open-ended and does not exclude additional unrecited elements, compositional components, or method steps. Accordingly, such term is intended to be synonymous with the words "has", "have", "having", "includes", "including", and any derivatives of these words.

As used herein, the terms "extensible" or "stretchable" mean elongatable in at least one direction, but not necessarily recoverable.

Unless otherwise indicated, percentages of components in formulations are by weight.

DETAILED DESCRIPTION OF THE INVENTION

Reference now will be made to the embodiments of the invention, one or more examples of which are set forth below. Each example is provided by way of explanation of the invention, not as a limitation of the invention. In fact, it will be apparent to those skilled in the art that various modifications and variations can be made in this invention without departing from the scope or spirit of the invention. For instance, features illustrated or described as part of one embodiment can be used on another embodiment to yield a still further embodiment.

Thus, it is intended that the present invention cover such modifications and variations as come within the scope of the appended claims and their equivalents. Other objects, features and aspects of the present invention are disclosed in or are obvious from the following detailed description. It is to be understood by one of ordinary skill in the art that the present discussion is a description of exemplary embodiments only, and is not intended as limiting the broader aspects of the present invention, which broader aspects are embodied in the exemplary constructions.

The presently described stretchable laminate articles can be utilized in a variety of applications such as in diapers and other products requiring a certain degree of elasticity. As described above, the elastic laminate articles have certain advantages over previously described stretchable laminate articles in that they provide increased level of latent elasticity.

For the purposes of this invention an elastic stretch bonded laminate includes at least one elastic core layer and at least one gatherable facing layer, the gatherable facing layer being laminated to the elastic core layer. The elastic core layer includes a first component including a first elastomeric polymer that may be, by way of example only, a styrenic block copolymer, a polyurethane polymer, and so forth. The elastic core layer further includes a second component including a single site catalyzed polyolefin. Desirably the elastic core layer includes an array of continuous filament strands with an optional meltblown fiber layer deposited on the continuous filament strands. The single site catalyzed polyolefin may be, for example, an elastic polyolefin-based polymer having a degree of crystallinity between about 3% and about 30%, or between about 5% and about 25%, or between about 5% and about 15%. The elastic polyolefin-based polymer may also have a melt flow rate between about 10 and about 600 grams per 10 minutes, or between about 60 and about 300 grams per 10 minutes, or between about 150 and about 200 grams per 10 minutes; a melting/softening point between about 40 and about 160 degrees Celsius; and/or a density from about 0.8 to about 0.95, or about 0.85 to about 0.90, or about 0.85 to about 0.87 grams per cubic centimeter. The elastic polyolefin-based polymer may include polyethylene, polypropylene, butene, or octene homo- or copolymers, ethylene methacrylate, ethylene vinyl acetate, butyl acrylate copolymers, or a combination of any of these polymers.

One example of a suitable elastic polyolefin-based polymer is VISTAMAXX elastomer, available from ExxonMobil Chemical Company of Houston, Tex. Other examples of suitable polyolefin-based polymers include EXACT plastomer, OPTEMA ethylene methacrylate, and VISTANEX polyisobutylene, and metallocene-catalyzed polyethylene, all available from ExxonMobil Chemical Company, as well as AFFINITY polyolefin plastomers, such as AFFINITY EG 8185, AFFINITY GA 1900, AFFINITY GA 1950, and VERSIFY propylene-ethylene copolymers available from Dow Chemical Company of Midland, Mich..; ELVAX ethylene vinyl acetate, available from E. I. Du Pont de Nemours and Company of Wilmington, Del.; and ESCORENE ULTRA ethylene vinyl acetate, available from ExxonMobil Chemical Company.

The single site catalyzed polyolefin suitably may have a relatively fast crystallization rate, with partial regions of crystalline and amorphous phases. In different embodiments, the second component including the single-site catalyzed elastic polyolefin-based polymer may be incorporated within the latently elastic core in a meltblown layer, continuous filament strands, a film, foam, or other structure within the latently elastic core.

As mentioned, the latently elastic core layer may include an array of continuous filament strands with a meltblown layer deposited on the continuous filament strands. Additional components may be included in the latently elastic core layer, such as a film, an elastic scrim or netting structure, a foam material, or a combination of any of the foregoing materials. If a film is used, it may be an apertured film. In certain embodiments, any of these additional components may be used in place of the array of continuous filament strands and/or the meltblown layer. The combination of a generally parallel series of elastomeric continuous filaments or strands (fiber array) and meltblown materials deposited on the filaments is described in previously noted U.S. Pat. No. 5,385,775 to Wright. The filament to meltblown basis weight ratio in such an elastic layer may be about 90:10, for example.

At least one of the components of the latently elastic core layer may be formed from an elastic polyolefin-based polymer having a degree of crystallinity between about 3% and about 40%, or between about 5% and about 30%, or between about 15% and about 25%, as described above. For example, the elastic polymer may be used to form the meltblown layer, a portion of the continuous filaments, or may be used as a second component in a conjugate filament arrangement. When the meltblown layer includes the elastic polyolefin-based polymer, the meltblown layer may be applied at an add-on up to about 34 gsm, or between about 1 and about 15 grams per square meter (gsm), or between about 5 and about 10 gsm. Inelastic meltblown tends to crack and form discrete islands as the strands stretch prior to lamination at higher add-on levels, which leads to non-uniformity. However, elastic meltblown does not suffer such drawbacks at higher add-on levels.

When present, the meltblown layer may be a multilayer component. In one embodiment, a multilayer meltblown includes at least one layer of a polymer blend including a styrenic block copolymer and at least one layer of a single site catalysis polyolefin.

As mentioned, the latently elastic core layer includes a first component that includes a thermoplastic elastomer. As one example, the thermoplastic elastomer may be a styrenic block copolymer. Block copolymers may have the general formula A-B-A' where A and A' are each a thermoplastic polymer endblock which contains a styrenic moiety such as a poly (vinyl arene) and where B is an elastomeric polymer midblock such as a conjugated diene or a lower alkene polymer.

Specific examples of useful styrenic block copolymers include hydrogenated polyisoprene polymers such as styrene-ethylenepropylene-styrene (SEPS), styrene-ethylenepropylene-styrene-ethylenepropylene (SEPSEP), hydrogenated polybutadiene polymers such as styrene-ethylenebutylene-styrene (SEBS), styrene-ethylenebutylene-styrene-ethylenebutylene (SEBSEB), styrene-butadiene-styrene (SBS), styrene-isoprene-styrene (SIS), and hydrogenated poly-isoprene/butadiene polymer such as styrene-ethylene-ethylenepropylene-styrene (SEEPS). Polymer block configurations such as diblock, triblock, multiblock, star and radial are also contemplated in this invention. In some instances, higher molecular weight block copolymers may be desirable. Block copolymers are available from KRATON Polymers U.S. LLC of Houston, Tex. under the designations KRATON G or D polymers, for example G-1652, G-1657M, G-1730, D-1114, D-1116, D-1102 and Septon Company of America, Pasadena, Tex. under the designations SEPTON 2004, SEPTON 4044, and SEPTON 4033. Other potential suppliers of such polymers include Dexco Polymers of Houston, Tex. and Dynasol of Houston, Tex. Blends of such elastomeric resin materials are also contemplated as the first component of the latently elastic core layer. Additionally, other desirable block copolymers are disclosed in U.S. Patent Application Publication 2003/0232928A1, which is incorporated by reference herein in its entirety.

Other exemplary thermoplastic elastomers which may be used include polyurethane elastomeric materials such as, for example, those available under the trademark ESTANE from Noveon, polyamide elastomeric materials such as, for example, those available under the trademark PEBAX (polyether amide) from Atofina Chemicals Inc., of Philadelphia, Pa., and polyester elastomeric materials such as, for example, those available under the trade designation HYTREL from E.I. DuPont De Nemours & Company.

Useful elastomeric polymers also include, for example, elastic polymers and copolymers of ethylene and at least one vinyl monomer such as, for example, vinyl acetates, unsaturated aliphatic monocarboxylic acids, and esters of such monocarboxylic acids. The elastic copolymers and formation of elastomeric meltblown fibers from those elastic copolymers are disclosed, for example, in U.S. Pat. No. 4,803,117, the entirety of which is incorporated herein by reference.

Such thermoplastic elastomer base resins may be further combined with tackifiers and/or processing aids in compounds. Processing aids that may be added to the elastomeric polymer described above include a polyolefin to improve the processability of the composition. The polyolefin must be one which, when so blended and subjected to an appropriate combination of elevated pressure and elevated temperature conditions, is extrudable, in blended form, with the elastomeric base polymer. Useful blending polyolefin materials include, for example, polyethylene, polypropylene and polybutylene, including ethylene copolymers, propylene copolymers and butene copolymers. A particularly useful polyethylene may be obtained from Eastman Chemical under the designation EPOLENE C-10. Additionally, the single site catalyzed polyolefin materials described above may be blended with the thermoplastic elastomer. Two or more of the polyolefins may also be utilized. Extrudable blends of elastomeric polymers and polyolefins are disclosed in, for example, U.S. Pat. No. 4,663,220 and U.S. Publication 2004/0127128, each of which is incorporated herein in its entirety by reference thereto.

The elastomeric filaments may have some tackiness/adhesiveness to enhance autogenous bonding. For example, the elastomeric polymer itself may be tacky when formed into films, and/or filaments or, alternatively, a compatible tackifying resin may be added to the extrudable elastomeric compositions described above to provide tackified elastomeric fibers and/or filaments that autogenously bond. In regards to the tackifying resins and tackified extrudable elastomeric compositions, note the resins and compositions as disclosed in U.S. Pat. No. 4,787,699, hereby incorporated by reference in its entirety.

Any tackifier resin can be used which is compatible with the elastomeric polymer and can withstand the high processing (e.g. extrusion) temperatures. If the elastomeric polymer (e.g. A-B-A elastomeric block copolymer) is blended with processing aids such as, for example, polyolefins or extending oils, the tackifier resin should also be compatible with those processing aids. Generally, hydrogenated hydrocarbon resins are desirable tackifying resins, because of their better temperature stability. REGALREZ series tackifiers are examples of such hydrogenated hydrocarbon resins. REGALREZ hydrocarbon resins are available from Eastman Chemical. Of course, the present invention is not limited to use of such tackifying resins, and other tackifying resins which are compatible with the other components of the composition and can withstand the high processing temperatures, can also be used. Other tackifiers are available from ExxonMobil under the ESCOREZ designation.

Typically, the blend used to form the web, film or filaments when such is made from an extruded material in an on-line process, includes for example, from about 40 to about 90 percent by weight elastomeric polymer base resin, from about 0 to about 40 percent polyolefin processing aid, and from about 5 to about 40 percent resin tackifier. These ratios can be varied depending on the specific properties desired and the polymers utilized. For an alternative embodiment, such blend includes between about 60 and 80 percent base resin, between about 5 to 30 percent processing aid, and between about 10 and 30 percent tackifier. In a further alternative embodiment, such blend includes a tackifier in an amount of between about 10 and 20 percent tackifier.

In some embodiments, it is advantageous to provide filaments from a die that can be configured such that the die holes provide alternating filaments of the two polymers to create an A-B-A-B pattern of filaments from the two polymers. For example, the A polymer can be a styrenic block copolymer or a blend including a styrenic block copolymer and the B polymer can be a single site catalysis elastic polyolefin.

In some embodiments, it is advantageous to provide fibers or filaments in the product that will consist of two polymers. Such fibers are typically known as using "bi-constituent" fibers. In one such configuration, one is allowed to select the components of fibers to be produced. For example, one may select a polymer "A" and a polymer "B" to provide a fiber blend in the final elasticized product or garment. In another embodiment, bi-component fibers (which typically have at least two separate types of fiber parts, usually in either a side-by-side or a sheath/core arrangement) might be utilized. For example, the A polymer can be a styrenic block copolymer or a blend including a styrenic block copolymer and the B polymer can be a single site catalysis elastic polyolefin. In a particularly desirable configuration, a styrenic block copolymer sheath is employed with a single site catalysis elastic polyolefin core.

The laminate further includes at least one gatherable facing layer laminated to the latently elastic core. The nonwoven web facing layer desirable gathers between points on its surface that are bonded to the latently elastic core. Essentially, those areas that are gathered are not bonded to the latently elastic core. While it is desirable that the gatherable layer be a nonwoven layer, such gatherable layer may also be a woven web, a cellulosic web as will later be described, a metallic foil-type layer or a combination of such. Such gatherable material may also be pretreated in some fashion prior to being bonded to the latently elastic core. Such pretreatments include for instance being necked. Such pretreatment may offer additional properties to the overall laminate material, such as bi or multidirectional stretch capabilities. Such gatherable layer may itself include multiple layers, and as such be a multilayered laminate.

The gatherable facing layer may be a nonwoven material such as, for example, one or more spunbonded webs (such as a conjugate fiber spunbond web), meltblown fiber webs, or bonded carded webs. An example of a spunbond web may be a polypropylene spunbond web having a basis weight of between about 0.3 and 0.8 osy. In one particular embodiment, a polypropylene spunbond facing having a basis weight of approximately 0.4 ounces per square yard ("osy") may be employed. In a further alternative embodiment, the spunbond web is necked between about 25 and 60 percent before it is bonded to the elastic layer. In still a further embodiment of the invention, the gatherable layer is a multilayer material having, for example, at least one layer of spunbond web joined to at least one layer of meltblown web, bonded carded web, or other suitable material. The gatherable layer may also be a composite material made of a mixture of two or more different fibers or a mixture of fibers and particulates, such as a coform material. Such mixtures may be formed by adding fibers and/or particulates to the gas stream in which meltblown fibers are carried so that an intimate entangled comingling of meltblown fibers and other materials, i.e. woodpulp, staplefibers and particulates such as, for example, hydrocolloid (hydrogel), particulates commonly referred to as superabsorbent materials, occurs prior to collection of the meltblown fibers upon a collecting device to form a coherent web of randomly dispersed meltblown fibers and other materials such as disclosed in U.S. Pat. No. 4,100,324 to Anderson et al., the disclosure of which is hereby incorporated by reference in its entirety. The facing layer may either be unwound from a roll or formed in-line.

The gatherable layer may be made of pulp fibers, including wood pulp fibers, to form a material such as, for example, a tissue layer. Additionally, the gatherable layer may be a layer or layers of hydraulically entangled fibers such as, for example hydraulically entangled mixtures of wood pulp and staple fibers such as disclosed, for example, in U.S. Pat. No. 4,781,966 to Taylor, the disclosure of which is hereby incorporated by reference in its entirety.

After formation of the elastic core material, the elastic core material may pass through a series of rollers and becoming stretched. For example, the elastic core material that includes the first component styrenic block copolymer and the second component single site catalyzed polyolefin plastomer may be conveyed to a laminator so that it may be bonded to the gatherable sheet material. Bonding may be achieved either autogenously or through the use of a separate adhesive or as a combination of autogenous and adhesive bonding. Typically, the process will have sufficiently quenched the elastic core material by the time it arrives at the bonding station so that autogenous (or bonding without adhesive) alone would not be possible without the presence of a tackifier in the elastic core material. In some embodiments, an adhesive, such as a melt-spray type adhesive, is employed.

In certain embodiments, the adhesive is sprayed directly onto the gatherable facing material to be bonded to the elastic core. However, other arrangements of adhesive application, such as brushing or the like, may also be utilized. In addition, the adhesive may be applied directly to the gatherable sheet material prior to bonding with the elastic core material, may be applied to both the elastic core material and the gatherable facing material prior to bonding, or may be applied to one or both of the elastic core material and the gatherable facing material while bonding pressure is being applied. The present invention is not limited to any particular bonding mechanism.

Particular meltspray adhesives that may be utilized include meltspray adhesives available from Bostik Inc. of Huntingdon Valley, Pa. These adhesives may be applied through a hot melt spray die at an elevated temperature of approximately 300-375° F. to the inner surface of the facing. The meltspray adhesive usually will form a very lightweight layer of about 3 grams per square meter ("gsm") of adhesive in the final composite. Desirably, the adhesives are elastic as well.

The system employs nip rolls to apply pressure to the adhesive-coating facing and the continuous filaments to result in the necessary lamination. The outer facing is bonded together with the continuous filaments at a fairly high surface pressure, which may be between about 20 and 300 pounds per linear inch ("pli"). A typical bonding pressure may be about 50 pli or about 100 pli.

Figure 1:
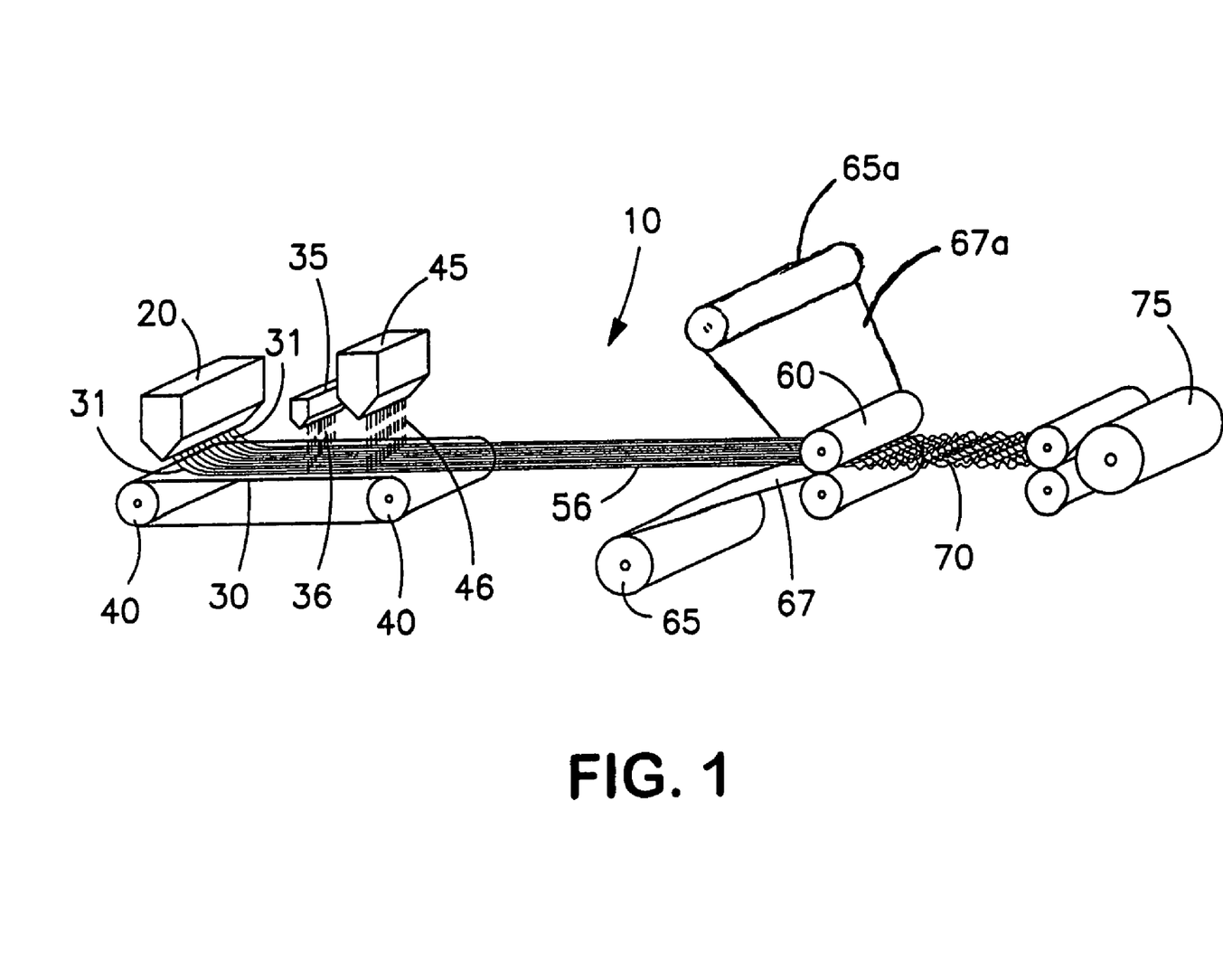
FIG. 1 illustrates a method of manufacturing a latently elastic stretch bonded laminate in accordance with the invention.

As can be seen in FIG. 1, which illustrates a schematic view of a method for manufacturing a latently elastic stretch bonded laminate material in accordance with the invention, FIG. 1 illustrates a horizontal, continuous filament laminate manufacturing process 10. A first extrusion apparatus 20 is fed with a polymer blend composition from one or more sources (not shown) which is extruded onto a forming surface 30 in filament form 31. The extruded polymer desirably includes a first component styrenic block copolymer elastomer and optionally includes a second component that includes an elastic polyolefin-based polymer. In various embodiments, a second extrusion apparatus 45 can be configured to produce other elastic materials, e.g. tackified elastic fibers 36. Techniques for fiber extrusion, such as modified meltblowing of the fibers, are further set forth in the previously mentioned U.S. Pat. No. 5,385,775 to Wright. Apparatus 20 extrudes filaments 31 directly onto a conveyor system, which can be a forming surface system 30 (e.g., a foraminous belt) moving clockwise about rollers 40. A vacuum (not shown) can also help hold the filaments 31 against the foraminous wire system. Optionally, a meltblown layer of an elastic polyolefin-based polymer may be extruded from an adjacent bank 35, such that the meltblown fibers 36 are placed on top of the continuous filaments 31 (array). The meltblown material is in one embodiment applied such that it represents 10 basis weight percent of the filament and meltblown structure, for example. In a particular embodiment, the elastic polyolefin-based polymer composition is the same in both the filaments and meltblown materials. In an alternative embodiment, the compositions are different (which may include the same base resin, but different percentages of processing aid or tackifiers).

The filament/meltblown laminate may be stretched by the differential speed of tensioning rollers (nip rolls) 60 to elongate and tension the filaments 56. Optionally, the laminate may be compacted, and tensioned, by an additional pair of rolls (not shown). The tension rollers are therefore operating at speeds which exceed the speed at which the meltblown covered filament array is exiting the forming surface. Desirably the tension rollers 60 are provided with a surface having little to no affinity for the filaments or fibers. In one embodiment, the filaments are stretched between about 3 and 6× from the forming surface to the tensioning rollers.

At the same time, one or more gatherable facing layers 67 is either made in line or unwound from a roll 65 and introduced into the set of nip rolls 60 with the filament array laminate such that the facing layers 67 are laminated to the elastic core. The gatherable facings are bonded to the elastic core while the elastic core is still being stretched. The filament array and facings then exit the nip 60 as a continuous filament elastic stretch bonded laminate. The elastic laminate 70 is then allowed to relax, forming gathers therein between bonding points on the facing layer, and is collected on a collection roll 75 for further use. The collection roll then winds the laminate, typically at a speed less than that of the nip rolls, such as between about 0.50 and 0.75 of the nip roll speeds. The nip rollers 60 may be desirably designed to provide a 100 percent bond area through the use of flat calender rolls or may provide a patterned bond area. The rollers 60 can be heated to a degree below the melting/softening points of the various laminate components, or may be ambient, or chilled.

Figure 2:
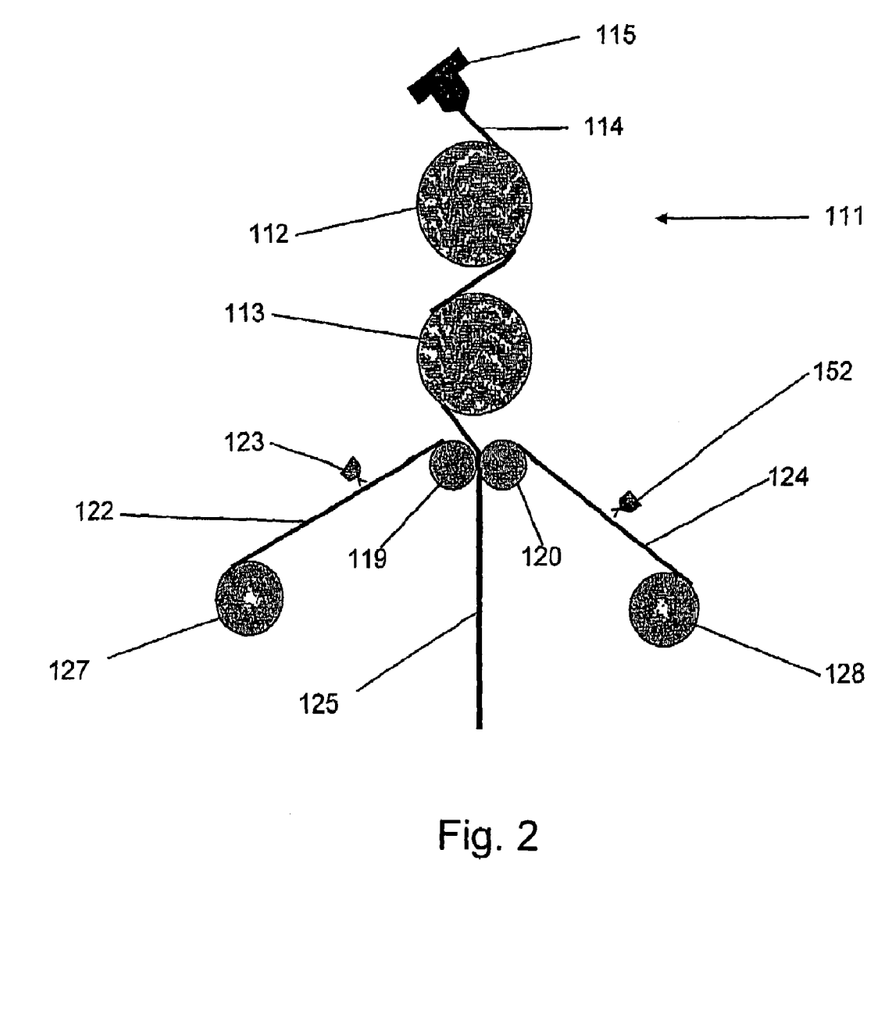
FIG. 2 illustrates an alternative method of manufacturing a latently elastic stretch bonded laminate in accordance with the invention.

In FIG. 2, an exemplary vertically arranged apparatus 111 for making latently elastic stretch bonded laminates is depicted. An extruder 115 is mounted for extruding continuous molten filaments 114 downward from a die at a canted angle onto chilled positioning roller 112. Chilled positioning roller 112 ensures proper alignment through the remainder of the system as it spreads the filaments. As the filaments travel over the surface of chilled positioning roller 112, they are cooled and solidified as they travel towards and over the chilled surface of chilled roller 113. As in other embodiments, the filaments then travel downward toward the laminator section of the system comprising a nip formed by nip roller 119 and nip roller 120, but in this instance, do so without the need for the series of s-wrap rollers described above. The continuous filaments in this embodiment may also be combined at the nip with various types of facings. In the embodiment depicted in FIG. 2, a first non-woven spunbond facing 122 and a second non-woven spunbond facing 124 are combined on opposing surfaces of the continuous filaments to form a bonded laminate 125. The spunbond facings 122 and 124 are provided to the nip by first outer facing roll 127 and second outer facing roll 128.

Bonding of the facings to the continuous filaments is accomplished in this embodiment by the use of two spray-type adhesive applicators. A spray head 123 delivers adhesive to the surface of at least one of the non-woven spunbond facings 122 prior to compression and lamination at the nip; and a second spray head 152 applies adhesive to the other non-woven spunbond facing 124. Vertically arranged systems for producing stretch bonded laminates are further described in U.S. Patent Application Publication 2002/0104608 to Welch et al., the entire content of which is incorporated herein by reference.

Figure 3:
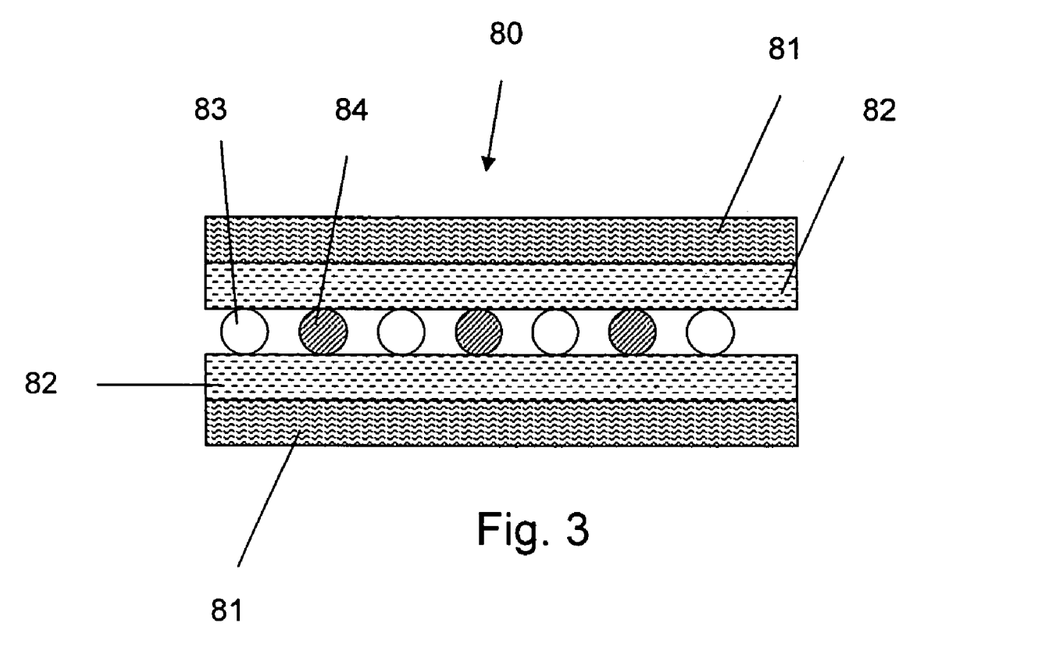
FIG. 3 illustrates a cross sectional view of one embodiment of a latently elastic stretch bonded laminate material.

One embodiment of a latently elastic stretch bonded laminate structure can be seen in FIG. 3 which illustrates a cross sectional stylistic view of a stretch bonded laminate 80 made in accordance with the invention. As can be seen in the figure, the stretch bonded laminate 80 includes first and second gatherable facings 81. First and second adhesive layers 82 adjacent and bonded to the gatherable facings 81 are situated adjacent and bonded to an array of first filaments 83 and second filaments 84. The first filaments 83 and second filaments 84 are shown in an A-B-A-B arrangement, but other similar arrangements may be used. Desirably, the first filaments 83 can be a styrenic block copolymer or a blend including a styrenic block copolymer and the second filaments 84 can be a single site catalysis elastic polyolefin. Optionally, an elastic meltblown layer (not shown) may be positioned between the filaments 83, 84 and one of the first and second adhesive layers 82.

Figure 4:
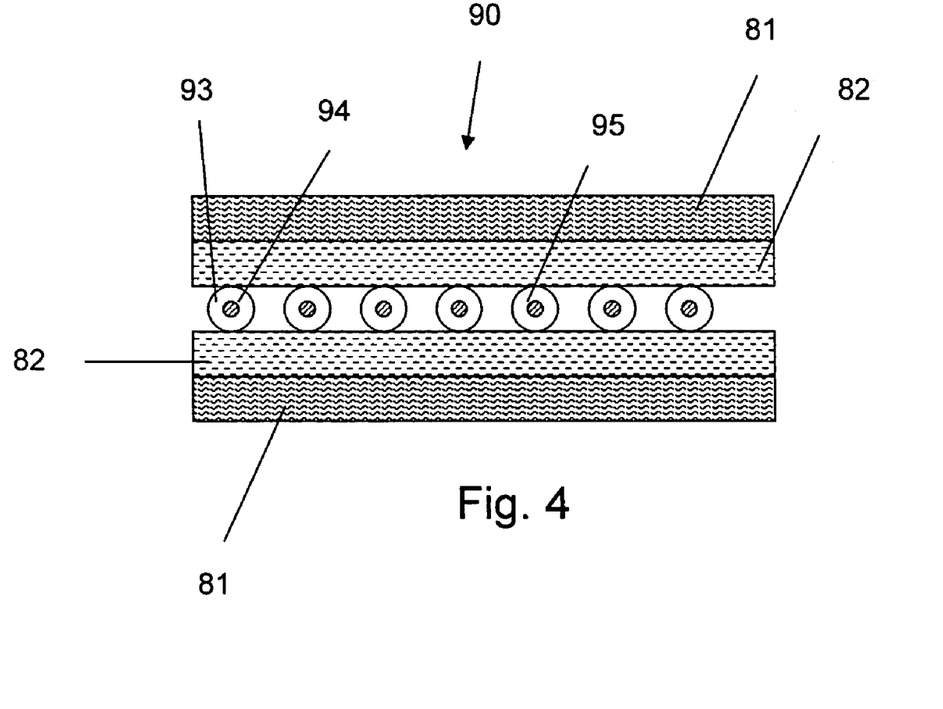
FIG. 4 illustrates a cross sectional view of another embodiment of a latently elastic stretch bonded laminate material.

In another embodiment, as illustrated in cross section in FIG. 4, a stretch bonded laminate 90 made in accordance with the invention includes sheath/core bicomponent filaments 95 including a sheath 93 and a core 94. The stretch bonded laminate 90 includes first and second gatherable facings 81. First and second adhesive layers 82 adjacent and bonded to the gatherable facings 81 are situated adjacent and bonded to the sheath/core filaments 95. In a particularly desirable configuration, a styrenic block copolymer or polymer blend containing a styrenic block copolymer is used as the sheath 93 and a single site catalysis elastic polyolefin is used as the core 94. While sheath/core bicomponent filaments are depicted in the figure, it is contemplated that other multicomponent configurations may be used, for example, a side by side configuration.

Figure 5:
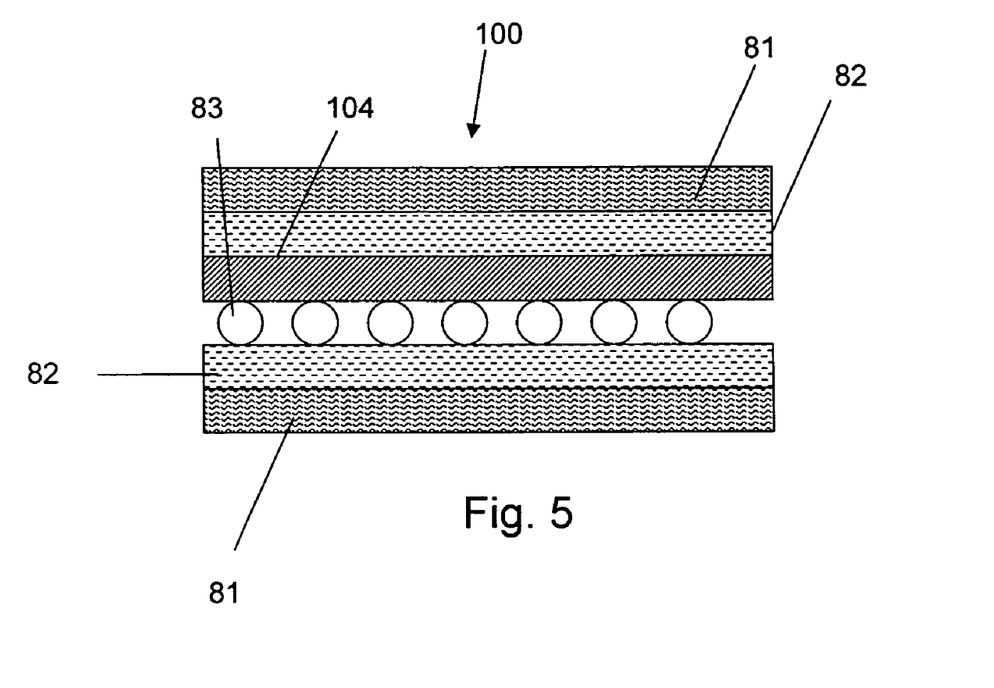
FIG. 5 illustrates a cross sectional view of yet another embodiment of a latently elastic stretch bonded laminate material.

In a further embodiment, as illustrated in cross section in FIG. 5, a stretch bonded laminate 100 made in accordance with the invention includes elastic filaments 83 and an adjacent elastic meltblown layer 104 bonded thereto. In a particularly desirable configuration, the elastic filaments 83 include a styrenic block copolymer or polymer blend containing a styrenic block copolymer and the meltblown layer 104 includes a single site catalysis elastic polyolefin. The stretch bonded laminate 100 includes first and second gatherable facings 81. First and second optional adhesive layers 82 adjacent and bonded to the gatherable facings 81 are situated adjacent and bonded to the filaments 83 and the meltblown layer 104.

In FIGS. 3, 4, and 5, the thicknesses of the various layers are not to scale, and are exaggerated to illustrate their existence. It should be recognized that while each of the various cross sections of these figures illustrate a relatively flat gatherable facing layer material 81, such gatherable facings are actually gathered between where they are bonded to the respective elastic layers, but for stylistic purposes, such web is shown in a relatively flat configuration.

In one embodiment, the continuous filaments in such laminates are desirably present in an amount between about 7 to 18, or about 8 to 15 filaments per cross-directional inch. The basis weight of the meltblown layers and/or the continuous filaments may be up to about 34 gsm, or between about 1 and 25 gsm, or between about 1 and 15 gsm, at the point of lamination. The basis weight of such gatherable facing materials is desirably between about 0.3 and 0.8 osy.

The latent elasticity of the stretch bonded laminate materials described herein may be quantified by a Heat Activated Retraction Test (HAR) that is described in detail below. In some embodiments, the materials of the present invention may demonstrate HAR values between about 10 and about 40 percent, between about 16 and about 31 percent, between about 16 and about 21 percent, between about 21 and about 31 percent, between about 18 and about 28 percent, between about 29 and about 36 percent, between about 29 and about 30 percent, between about 34 and about 36 percent, between about 31 and 37 percent, and so forth.

Such latently elastic stretch bonded laminate materials as described herein have particular effectiveness for use in personal care products. Such latently elastic materials may be more easily processed into personal care products because they are less elastic than similar materials not being latently elastic. However, once in the final product, the latently elastic materials may be heat activated to provide target levels of elasticity.

Such latently elastic stretch bonded laminate materials may be useful in providing elastic waist, leg cuff/gasketing, stretchable ear, side panel or stretchable outer cover applications. While not intending to be limiting, FIG. 6 is presented to illustrate the various components of a personal care product, such as a diaper, that may take advantage of such latently elastic stretch bonded laminate materials. Other examples of personal care products that may incorporate such materials are training pants (such as in side panel materials) and feminine care products. By way of illustration only, training pants suitable for use with the present invention and various materials and methods for constructing the training pants are disclosed in U.S. Pat. No. 6,761,711 to Fletcher et al.; U.S. Pat. No. 4,940,464 to Van Gompel et al.; U.S. Pat. No. 5,766,389 to Brandon et al.; and U.S. Pat. No. 6,645,190 to Olson et al., which is each incorporated herein by reference in its entirety.

With reference to FIG. 6, a disposable diaper 250 generally defines a front waist section 255, a rear waist section 260, and an intermediate section 265 which interconnects the front and rear waist sections. The front and rear waist sections 255 and 260 include the general portions of the diaper which are constructed to extend substantially over the wearer's front and rear abdominal regions, respectively, during use. The intermediate section 265 of the diaper includes the general portion of the diaper that is constructed to extend through the wearer's crotch region between the legs. Thus, the intermediate section 265 is an area where repeated liquid surges typically occur in the diaper.

The diaper 250 includes, without limitation, an outer cover, or backsheet 270, a liquid permeable bodyside liner, or topsheet, 275 positioned in facing relation with the backsheet 270, and an absorbent core body, or liquid retention structure, 280, such as an absorbent pad, which is located between the backsheet 270 and the topsheet 275. The backsheet 270 defines a length, or longitudinal direction 286, and a width, or lateral direction 285 which, in the illustrated embodiment, coincide with the length and width of the diaper 250. The liquid retention structure 280 generally has a length and width that are less than the length and width of the backsheet 270, respectively. Thus, marginal portions of the diaper 250, such as marginal sections of the backsheet 270 may extend past the terminal edges of the liquid retention structure 280. In the illustrated embodiments, for example, the backsheet 270 extends outwardly beyond the terminal marginal edges of the liquid retention structure 280 to form side margins and end margins of the diaper 250. The topsheet 275 is generally coextensive with the backsheet 270 but may optionally cover an area which is larger or smaller than the area of the backsheet 270, as desired.

To provide improved fit and to help reduce leakage of body exudates from the diaper 250, the diaper side margins and end margins may be elasticized with suitable elastic members, as further explained below. For example, as representatively illustrated in FIG. 6, the diaper 250 may include leg elastics 290 which are constructed to operably tension the side margins of the diaper 250 to provide elasticized leg bands which can closely fit around the legs of the wearer to reduce leakage and provide improved comfort and appearance. Waist elastics 295 are employed to elasticize the end margins of the diaper 250 to provide elasticized waistbands. The waist elastics 295 are configured to provide a resilient, comfortably close fit around the waist of the wearer.

The latently elastic stretch bonded laminate materials of the inventive structure are suitable for use as the leg elastics 290 and waist elastics 295. Exemplary of such materials are laminate sheets which either comprise or are adhered to the backsheet, such that elastic constrictive forces are imparted to the backsheet 270.

As is known, fastening means, such as hook and loop fasteners, may be employed to secure the diaper 250 on a wearer. Alternatively, other fastening means, such as buttons, pins, snaps, adhesive tape fasteners, cohesives, fabric-and-loop fasteners, or the like, may be employed. In the illustrated embodiment, the diaper 250 includes a pair of side panels 300 (or ears) to which the fasteners 302, indicated as the hook portion of a hook and loop fastener, are attached. Generally, the side panels 300 are attached to the side edges of the diaper in one of the waist sections 255, 260 and extend laterally outward therefrom. The side panels 300 may be elasticized or otherwise rendered elastomeric by use of a latently elastic stretch bonded laminate materials made from the inventive structure. Examples of absorbent articles that include elasticized side panels and selectively configured fastener tabs are described in PCT Patent Application WO 95/16425 to Roessler; U.S. Pat. No. 5,399,219 to Roessler et al.; U.S. Pat. No. 5,540,796 to Fries; and U.S. Pat. No. 5,595,618 to Fries each of which is hereby incorporated by reference in its entirety.

The diaper 250 may also include a surge management layer 305, located between the topsheet 275 and the liquid retention structure 280, to rapidly accept fluid exudates and distribute the fluid exudates to the liquid retention structure 280 within the diaper 250. The diaper 250 may further include a ventilation layer (not illustrated), also called a spacer, or spacer layer, located between the liquid retention structure 280 and the backsheet 270 to insulate the backsheet 270 from the liquid retention structure 280 to reduce the dampness of the garment at the exterior surface of a breathable outer cover, or backsheet, 270. Examples of suitable surge management layers 305 are described in U.S. Pat. No. 5,486,166 to Bishop and U.S. Pat. No. 5,490,846 to Ellis.

As representatively illustrated in FIG. 6, the disposable diaper 250 may also include a pair of containment flaps 310 which are configured to provide a barrier to the lateral flow of body exudates. The containment flaps 310 may be located along the laterally opposed side edges of the diaper adjacent the side edges of the liquid retention structure 280. Each containment flap 310 typically defines an unattached edge which is configured to maintain an upright, perpendicular configuration in at least the intermediate section 265 of the diaper 250 to form a seal against the wearer's body. The containment flaps 310 may extend longitudinally along the entire length of the liquid retention structure 280 or may only extend partially along the length of the liquid retention structure. When the containment flaps 310 are shorter in length than the liquid retention structure 280, the containment flaps 310 can be selectively positioned anywhere along the side edges of the diaper 250 in the intermediate section 265. Such containment flaps 310 are generally well known to those skilled in the art. For example, suitable constructions and arrangements for containment flaps 310 are described in U.S. Pat. No. 4,704,116 to K. Enloe.

The diaper 250 may be of various suitable shapes. For example, the diaper may have an overall rectangular shape, T-shape or an approximately hour-glass shape. In the shown embodiment, the diaper 250 has a generally I-shape. Other suitable components which may be incorporated on absorbent articles of the present invention may include waist flaps and the like which are generally known to those skilled in the art. Examples of diaper configurations suitable for use in connection with the latently elastic stretch bonded laminate materials of the instant invention which may include other components suitable for use on diapers are described in U.S. Pat. No. 4,798,603 to Meyer et al.; U.S. Pat. No. 5,176,668 to Bernardin; U.S. Pat. No. 5,176,672 to Bruemmer et al.; U.S. Pat. No. 5,192,606 to Proxmire et al. and U.S. Pat. No. 5,509,915 to Hanson et al. each of which is hereby incorporated by reference in its entirety.

The various components of the diaper 250 are assembled together employing various types of suitable attachment means, such as adhesive bonding, ultrasonic bonding, thermal point bonding or combinations thereof. In the shown embodiment, for example, the topsheet 275 and backsheet 270 may be assembled to each other and to the liquid retention structure 280 with lines of adhesive, such as a hot melt, pressure-sensitive adhesive. Similarly, other diaper components, such as the elastic members 290 and 295, fastening members 302, and surge layer 305 may be assembled into the article by employing the above-identified attachment mechanisms.

It should be appreciated that such latently elastic stretch bonded laminate materials may likewise be used in other personal care products, protective outerwear, protective coverings and the like. Further such materials can be used in bandage materials for both human and animal bandaging products. Use of such materials provides the same manufacturing benefits described above.

The present invention may be better understood by reference to the Examples below. However, it is to be understood that the invention is not limited thereto.

Test Methods

Heat Activated Retraction (HAR) Latency Test

To measure heat-activated retraction, marks spaced 100 mm apart are placed on the material while the material is still under tension on the roll. The material is then released from tension on the roll and a length of material containing the marks is cut from the roll. Immediately after releasing the material and cutting it, the distance between the marks is measured again to determine the initial length (Before Heated Retraction Length or BHRL). The material is then submerged in 160° F. water for at least 30 seconds, but no more than 1 minute. Thereafter, the distance between the marks is again measured (After Heated Retraction Length or AHRL). The HAR, which is indicative of the latent elasticity of the material, is then calculated by the following equation:

HAR=(BHRL−AHRL)×100/BHRL

Generally, three measurements are averaged for each sample to be tested.

EXAMPLES

Example 1

In one example, two extruders were used to extrude parallel continuous filaments onto a chilled roll. In the first extruder, a thermoplastic elastomer blend containing a styrenic block copolymer was extruded into parallel continuous filaments. Samples were made using two different thermoplastic elastomer blends. Blend #1 contained about 68 percent KRATON® G-1730 styrene-ethylenepropylene block copolymer available from KRATON Polymers LLC, about 12 percent C-10 polyethylene wax, and about 20 percent REGALREZ® 1126 tackifier, both being available from Eastman Chemical. Blend #2 contained about 80 percent KRATON® G-1730 styrene-ethylenepropylene block copolymer, about 7 percent C-10 polyethylene wax, and about 13 percent REGALREZ® 1126 tackifier. In the second extruder, a single-site catalysis elastomeric polyolefin was extruded into parallel continuous filaments. The single-site catalysis elastomeric polyolefin was a polyolefin plastomer identified as Dow AFFINITY EG 8185, available from The Dow Chemical Company of Midland, Mich. The extruders were arranged such that the different types of continuous filaments were distributed in an A-B-A-B arrangement on the chilled roll. That is, the different filaments alternated across the face of the chilled roll. The weight percents of the filaments and the overall basis weight of the filaments varied as shown in Table 1 below. The filaments were quenched on the chilled roll, and were then stretched by 350% before being laminated between two spunbond facings at 100 feet per minute. Bostik 2808 adhesive, available from Bostik, Inc., was sprayed on the spunbond facings to bond the laminate together. The laminate was wound up at a speed 63 feet per minute, thus allowing retraction to occur. Samples were cut and tested as described above in the Heat Activated Latency Test. Results are provided in Table 1 below. As can be seen in Table 1, latent elasticity is demonstrated by heat activation relaxations ranging from 11% to 31%.

TABLE 1

| Sample | Blend | AFFINITY Percent | Blend Percent | Basis Weight | BHRL | AHRL | % HAR |
|---|---|---|---|---|---|---|---|
| 1 | 1 | 75 | 25 | 20 | 96 | 66 | 31% |
| 2 | 2 | 50 | 50 | 20 | 94 | 68 | 28% |
| 3 | 2 | 50 | 50 | 20 | 89 | 67 | 25% |
| 4 | 2 | 100 | 0 | 10 | 97 | 75 | 23% |
| 5 | 1 | 100 | 0 | 10 | 97 | 75 | 23% |
| 6 | 2 | 75 | 25 | 20 | 93 | 73 | 22% |
| 7 | 2 | 100 | 0 | 20 | 93 | 72 | 22% |
| 8 | 2 | 100 | 0 | 10 | 96 | 75 | 22% |
| 9 | 2 | 25 | 75 | 20 | 81 | 63 | 22% |
| 10 | 1 | 100 | 0 | 20 | 93 | 72 | 22% |
| 11 | 1 | 100 | 0 | 10 | 96 | 75 | 22% |
| 12 | 2 | 75 | 25 | 20 | 98 | 77 | 22% |
| 13 | 1 | 75 | 25 | 20 | 98 | 77 | 21% |
| 14 | 1 | 0 | 100 | 10 | 86 | 69 | 20% |
| 15 | 1 | 0 | 100 | 10 |  | 63 | 20% |
| 16 | 1 | 25 | 75 | 20 | 85 | 68 | 20% |
| 17 | 1 | 100 | 0 | 20 | 97 | 79 | 18% |
| 18 | 2 | 100 | 0 | 20 | 96 | 75 | 18% |
| 19 | 2 | 0 | 100 | 20 |  |  | 18% |
| 20 | 2 | 25 | 75 | 20 | 81 | 67 | 18% |
| 21 | 1 | 50 | 50 | 20 | 91 | 75 | 18% |
| 22 | 1 | 50 | 50 | 20 | 91 | 75 | 18% |
| 23 | 1 | 25 | 75 | 20 |  | 66 | 16% |
| 24 | 1 | 0 | 100 | 20 |  |  | 15% |
| 25 | 1 | 0 | 100 | 20 | 85 | 72 | 15% |
| 26 | 2 | 0 | 100 | 10 | 78 | 68 | 12% |
| 27 | 2 | 0 | 100 | 20 | 75 | 67 | 11% |
| 28 | 2 | 0 | 100 | 10 |  |  | 11% |

Example 2

In a second example, elastic laminates were produced from bicomponent continuous filaments extruded in a parallel arrangement onto a chilled roller. Two different polymers were processed through two separate extruders and through use of distribution plates, the two polymer streams were joined to form sheath/core filaments. The filament die had 12 holes per inch with each hole having a 0.9 mm diameter. Polymer throughput was varied through each extruder to achieve different polymer ratios in the filaments. It was verified under the microscope that sheath/core structures were being created. The filaments were extruded onto a large chill roll to quench the filaments. The filaments were then stretched in the machine direction by about 500%. The filaments were then adhesively laminated between two 0.4 osy spunbond facings. The adhesive (2 gsm melt spray adhesive 2808-08 available from Bostik, Inc.) was applied to one facing material prior to the nip point where all 3 components come together. No adhesive was used on the other facing. The material was then allowed to retract 45% at the winder. A third thermoplastic elastomer blend (Blend #3) was used in combination with both Dow AFFINITY EG8185 metallocene polyolefin plastomer and a thermoplastic polyurethane elastomer (TPU) available from Noveon. Blend #3 contained about 63 percent KRATON® G1659 styrene-ethylenebutylene-styrene block copolymer available from KRATON Polymers LLC, about 20 percent C-10 polyethylene wax, and about 17 percent REGALREZ® 1126 tackifier, both being available from Eastman Chemical. As can be seen in Table 2, increased latent elasticity is demonstrated by bicomponent structure containing the polyolefin plastomer.

TABLE 2

| Sample | Blend | Other Polymer | Blend Percentage | BHRL | AHRL | % HAR |
|---|---|---|---|---|---|---|
| 29 | 3 | EG8185 | 85 | 94 | 60 | 36% |
| 30 | 3 | EG8185 | 15 | 95 | 63 | 34% |
| 31 | 3 | TPU | 85 | 86 | 60 | 30% |
| 32 | 3 | TPU | 15 | 85 | 60 | 29% |

Example 3

In a third example, elastic laminates having elastic cores of both parallel continuous filaments and meltblown fibers were produced. In one sample, Blend #1 from Example 1 was used in the continuous filaments and Dow AFFINITY EG8185 polyolefin plastomer was used for the meltblown fibers. In the other sample, Blend #1 from Example 1 was used in both the meltblown and the continuous filaments. The filament die had 12 holes per inch, each hole having 0.9 mm diameter. The filaments were first laid down on a foraminous wire and then the meltblown was formed on top of the filaments. The basis weight on the wire of the elastic core was 20 gsm, with the filaments having a basis weight of 12 gsm and the meltblown having a basis weight of 8 gsm.

The elastic filament/MB structure was removed from the forming wire and stretched in the machine direction before being laminated between 0.40 osy spunbond facings via smooth roll calendering. The laminate was then wound on a roll at a speed slower than that of the of the smooth roll calendar, thus allowing the laminate to retract. The process conditions and heat activated retraction test results are summarized in Table 3. As can be seen in Table 3, increased latent elasticity is demonstrated by the structure containing the polyolefin plastomer.

TABLE 3

| Sample | Filament Blend | MB Polymer | Stretch Ratio | Retraction at Winder | BHRL | AHRL | % HAR |
|---|---|---|---|---|---|---|---|
| 33 | 1 | EG8185 | 4.5 | 30% | 86 | 54 | 37% |
| 34 | 1 | Blend 1 | 5.0 | 25% | 86 | 60 | 30% |

Although preferred embodiments of the invention have been described using specific terms, devices, and methods, such description is for illustrative purposes only. The words used are words of description rather than of limitation. It is to be understood that changes and variations may be made by those of ordinary skill in the art without departing from the spirit or the scope of the present invention, which is set forth in the following claims. In addition, it should be understood that aspects of the various embodiments may be interchanged either in whole or in part. Therefore, the spirit and scope of the appended claims should not be limited to the description of the preferred versions contained therein. Further, it is recognized that many embodiments may be conceived that do not achieve all of the advantages of some embodiments, yet the absence of a particular advantage shall not be construed to necessarily mean that such an embodiment is outside the scope of the present invention. Moreover, it should be noted that any given range presented herein is intended to include any and all lesser included ranges. For example, a range of from 45-90 would also include 50-90; 45-80; 46-89 and the like. Thus, the range of 95% to 99.999% also includes, for example, the ranges of 96% to 99.1%, 96.3% to 99.7%, and 99.91% to 99.999%, etc.

What is claimed is:

1. A composite nonwoven fabric having latent elasticity, the composite nonwoven fabric comprising:
   a latently elastic core comprising first filaments comprising a styrenic block copolymer and second filaments consisting essentially of a single site catalyzed polyolefin, and
   at least one gatherable facing material laminated to the elastic core.

2. The composite nonwoven fabric having latent elasticity of claim 1, wherein the first filaments are continuous filaments substantially oriented in a machine direction of the latently elastic core.

3. The composite nonwoven fabric having latent elasticity of claim 1, wherein the second filaments are continuous filaments substantially oriented in a machine direction of the latently elastic core.

4. The composite nonwoven fabric having latent elasticity of claim 1, wherein the second filaments are meltblown filaments.

5. A personal care product comprising the composite nonwoven fabric having latent elasticity of claim 1.

6. The personal care product of claim 5, wherein the first filaments are continuous filaments substantially oriented in a machine direction of the latently elastic core.

7. The personal care product of claim 5, wherein the second filaments are continuous filaments substantially oriented in a machine direction of the latently elastic core.

8. The personal care of claim 5, wherein the second filaments are meltblown filaments.

* * * * *